(12) United States Patent
Roser et al.

(10) Patent No.: US 6,623,762 B2
(45) Date of Patent: *Sep. 23, 2003

(54) COMPOSITION AND METHOD FOR CONTROLLED RELEASE INJECTIONS

(75) Inventors: Bruce Joseph Roser, Cambridge (GB); Arcadio Garcia De Castro, Madrid (ES)

(73) Assignee: Cambridge Biostability Ltd., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/784,153

(22) Filed: Feb. 16, 2001

(65) Prior Publication Data

US 2002/0155129 A1 Oct. 24, 2002

(51) Int. Cl.$^7$ ............................. A61K 9/34; A61K 9/36; A61K 9/38; A61K 9/50; A61K 9/52; A61K 9/58; A61K 9/60; A61K 9/62; A61K 9/64; A61K 9/66; B32B 15/16

(52) U.S. Cl. ........................ 424/489; 424/493; 424/499; 424/500; 424/501; 428/402.21

(58) Field of Search ................................ 424/499, 500, 424/501, 493, 502, 489; 428/402.21; 514/53, 23

(56) References Cited

U.S. PATENT DOCUMENTS

| | | | |
|---|---|---|---|
| 4,698,318 A | 10/1987 | Vogel et al. | 501/10 |
| 5,270,048 A | 12/1993 | Drake | 424/426 |
| 5,562,608 A | 10/1996 | Sekins et al. | 604/20 |
| 5,698,318 A | 12/1997 | Burton et al. | 528/355 |
| 6,190,701 B1 | 2/2001 | Roser et al. | 424/499 |
| 6,290,991 B1 * | 9/2001 | Roser et al. | 424/502 |
| 2001/0038858 A1 * | 11/2001 | Roser et al. | 424/488 |

FOREIGN PATENT DOCUMENTS

| | | | |
|---|---|---|---|
| EP | 0383569 A2 | 8/1990 | |
| WO | WO90/11756 | 10/1990 | |
| WO | WO98/41188 | 9/1998 | |
| WO | WO99/47174 | 9/1999 | |
| WO | WO01/37804 | 5/2001 | |

OTHER PUBLICATIONS

DK Xing et al., Biologicals, vol. 24(1), Estimation of antigenic tetanus toxoid extracted. . ., pp. 1, Mar. 1996.
Jodar et al, Genetic Engineering News, Revolutionzing Immunizations, pp. 5 pages, Feb. 15, 1998.
World Health Organization Technical Report Series No. 595, Immunological Adjuvants, 40 pages, 1976.
J. Lloyd, Department of Vaccines and Biologicals, Tehcnologies for Vaccine delivery in the 21$^{st}$ century, 25 pages, 2000.
Morbidity and Mortality Weekly Report, vol. 43, No. RR–1, General Recommendations on Immunization, 40 pgs., Jan. 28, 1994.
Global Programme for Vaccines and Immunization, Safety of injections in immunization programmes, 8 pages, Oct. 1998.
J. Freund, Ann. Rev. Microbiol. 1, Some Aspects of Active Immunization, pgs. 291–308, 1947.

* cited by examiner

Primary Examiner—James Housel
Assistant Examiner—Shanon A Foley
(74) Attorney, Agent, or Firm—Jacobson Holman PLLC

(57) ABSTRACT

The present invention is a pharmaceutical composition and method for controlling the release of a drug or vaccine to a patient where a slow, controlled release of drug or antigen occurs over a considerable period of time after injection. The drug or vaccine is contained in sugar glass microspheres and then placed in an anhydrous liquid, preferably perfluorocarbon, so that the vaccine is protected against dissolution while remaining surrounded by anhydrous liquid. This simple non-toxic system, deliverable by current syringe or present or future needle-free systems, is inexpensive and reliable and aids in parenteral drug delivery or mass immunization campaigns by reducing the need for repeated injections.

19 Claims, 2 Drawing Sheets

COMPOSITION AND METHOD FOR CONTROLLED RELEASE INJECTIONS

FIELD OF THE INVENTION

Figure 1:
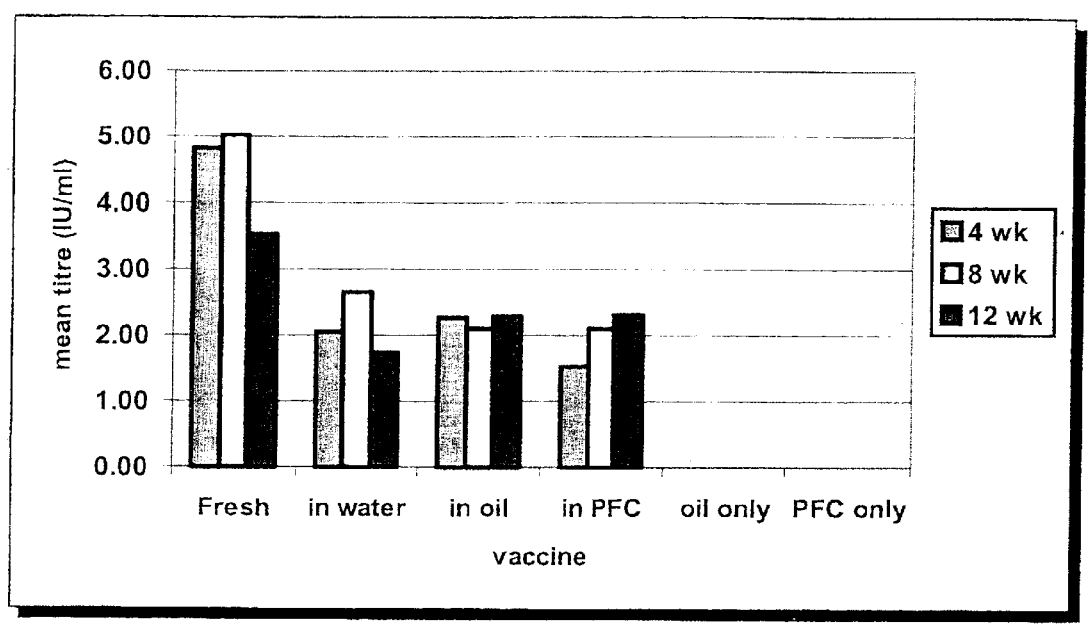
Figure 2:
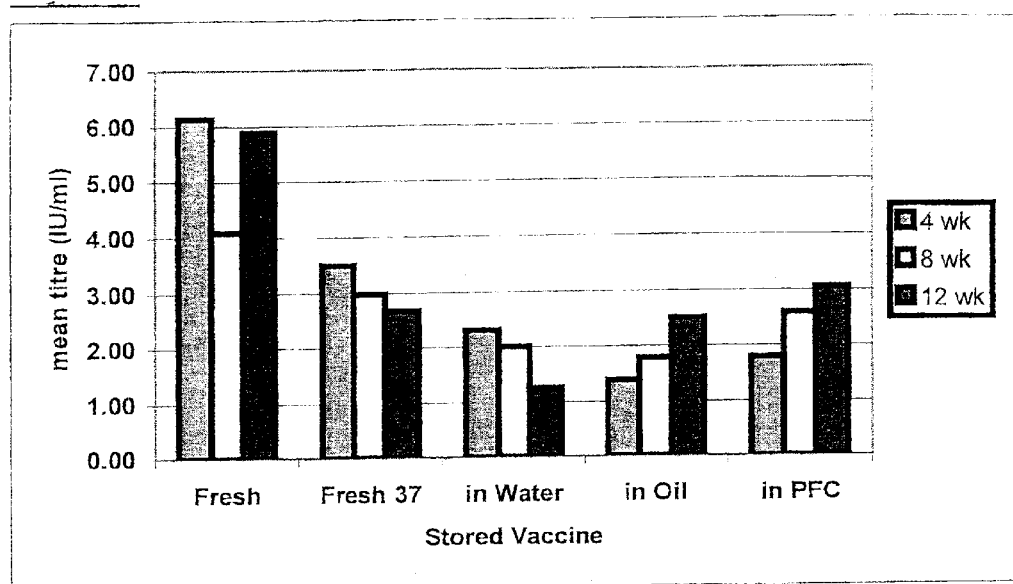

This invention relates generally to methods for controlled release of injected drugs and more specifically to controlled release vaccinations, which extend the duration of action of injected drugs or the duration of triggering of the immune response long after infection by slowly releasing the drug or vaccine into the circulatory system.

BACKGROUND OF THE INVENTION

Currently, vaccinations include the need for multiple injections over time in order to generate a protective memory immune response. Because the immune system responds only modestly to initial contact with antigens, repeat injections are necessary. Immunity is an adaptive or learned process in which each subsequent exposure to antigen elicits a stronger antibody response. The response is stronger, not only in the quantity of antibody made but also in the average affinity (the strength of attachment or binding of the antibody for the antigen.) Affinity increases because only those B cells which possess high-affinity receptors are selectively triggered to proliferation and survival in the later stages of the immune response as the concentration of antigen falls. Early after injection, of course, the concentration of antigen is high enough to trigger both high and low affinity receptors. With repeated antigen injections, a greater number of the specific antibody forming B lymphocytes are produced by this enhanced proliferation and survival as "memory" cells and the quantity of antibody therefore increases.

Typically, a childhood vaccination protocol for diphtheria, tetanus and pertussis (DTP) requires a priming dose of vaccine at 2 months of age, a first booster injection at 4 months of age, a second booster at 6 months of age another dose at 15–18 months, and a recommended final dose at 4–6 years of age (Centers for Disease Control and Prevention, National Immunization Program.) Other vaccines require similar protocols. These vaccine injections cause pain and distress, especially in infants; therefore, child-care providers often fail to return with the children for later injections. As a result, the immunization protocol is compromised and children are not properly protected against disease. The World Health Organization (WHO) identified this failure of compliance as a widespread occurrence resulting in jeopardising mass immunization campaigns. (Jodar L., Aguado T., Lloyd J. and Lambert P-H (1998) Revolutionizing Immunizations *Gen. Eng. News* 18 p. 6.)

In order to address this problem, considerable efforts have been made to develop techniques which reduce the number of injections required. One approach is controlled release vaccines, which extend the duration of triggering the immune response long after each injection, by slowly releasing the vaccine into the circulation. Most of the work to date addresses the tetanus vaccine encapsulated in bio-erodible plastic micro-spheres of poly lactide/glycoloide polymers [(Xing D. K. L., McLellan K., Corbel M. J., and Sesardic D. (1996) Estimation of antigenic tetanus toxoid extracted from biodegradable microspheres. *Biologicals* 24, 57–65.] The biodegradable plastics slowly solubilize in body fluids thereby releasing vaccine gradually from the eroded hydrophobic particles after injection. However, the vaccines were found to be unstable in the body, therefore, early results were disappointing, but newer formulations overcame these problems and tetanus vaccine now works reasonably well in this system. Other fragile vaccines, however, are not stable in plastic particles in the body at 37° C. It is for this reason that no other controlled release vaccine is currently in use.

In the course of developing stable liquids for injection, [(U.S. patent application Ser. No. 09/271,204 Composition and method for stable injectable liquids] stabilized formulations of tetanus vaccine in soluble, sugar glass microspheres suspended in anhydrous oils or perfluorocarbon liquids were studied. The stabilizing agent used was a soluble glass of the sugar alcohol mannitol which, upon contact with body water, it was expected to dissolve immediately and release its vaccine as a conventional priming dose. In pre-clinical testing, the stable liquid formulations were injected subcutaneously into groups of 10 guinea pigs. Dried vaccine was tested soon after manufacture (FIG. 1) and after it had been tested for stability by 3 months of accelerated aging at 37° C. (FIG. 2).

Aliquots of dry vaccine, stabilized in sugar glass, were dissolved in water before injection and served as controls as well as fresh source vaccine as the standard biological control vaccine preparation. Antibody responses were measured at 4, 8, and 12 weeks after injection.

It was found that all the control vaccines produced the typical kinetic response of antibody titer after a priming dose, specifically, the antibody levels peaked at 4–8 weeks and then fell by 12 weeks. However, when both groups were injected with stabilized vaccine in glass microspheres suspended in anhydrous biocompatible liquids, the antibody levels in these animals continued to rise throughout the whole of the 12 weeks after injection. This result, not seen before in guinea pig tetanus toxoid immunization indicated a distinct change in the kinetics of antibody production. When compared with the historical results of antibody kinetics studies in guinea pigs infected with repeated doses of standard vaccine, the present studies indicated controlled release of antigen. The rising antibody levels seen in the present study at 12 weeks indicated protection of the animals equivalent to that seen after a multiple infection course of standard soluble vaccine.

While sugar glasses have proven to be efficacious in providing a stable milieu for fragile biological molecules, other water-soluble glasses such as the metal carboxylates and similar glasses (Slow Release Vitreous Systems PCT No. WO 90/11756) and the phosphate glasses (Phosphate Glass Ceramics for Biological na Medical Applications U.S. Pat. No 4,698,318) can also be formulated as glass microspheres, either in combination with sugar glasses or separately (Amorphous glasses for stabilizing sensitive products. PCT application WO 99/47174) and have other desirable properties which suit them for use in this system. This includes the ability to pre-determine the rate at which the glass dissolves by formulating it from a mixture of salts with individually different solubility rates in water (Controlled Delivery Devices U.S. Pat. No. 5,270,048).

The stable liquid formulations in anhydrous biocompatible liquids were initially developed to solve two major problems, namely the need to refrigerate drugs or vaccines for storage and the need to reconstitute them in the field with sterile water before injection. Not only does the technology clearly overcome these drawbacks, it appears that these formulations in anhydrous liquids also solve the compliance problem. A convenient/ready-to-inject, stable vaccine provides a complete course of immunization with a single injection in the present invention.

It is hypothesized that some of the soluble glass microspheres containing the stabilized vaccine are protected against dissolution in body water by remaining surrounded by anhydrous liquid. They dissolve only at some time after injection to release their vaccine, which then acts as a booster dose giving rising levels of antibody throughout the whole 12 weeks of the experiment.

A lower average antibody level at 4 weeks exists with anhydrous liquid preparations than with soluble antigen. This lower early titer in the groups given anhydrous liquid suspensions of vaccine is arguably the result of a lower dose of antigen being released soon after injection. Some may argue this indicates a problem of delayed onset of immunity, however the protective level of antibody in this system is approximately 0.1 international units per milliliter of blood. The levels seen in the guinea pigs at 4 weeks were more than 1 international unit per milliliter, well above the protective level even at such an early stage.

BRIEF SUMMARY OF THE INVENTION

The present invention is a composition and method for controlled-release injections using soluble glass microspheres suspended in anhydrous liquids such as oils, silicone fluids or perfluorocarbons where a slow, controlled dissolution of the microspheres and release of antigen occurs over a considerable period of time after injection.

For a better understanding o f the present invention, together with other and further objects thereof, reference is made to the following description, taken in conjunction with the accompanying drawings, and its scope will be pointed out in the appending claims.

BRIEF DESCRIPTION OF THE DRAWINGS

FIG. 1 is a view of mean antibody titers of groups of 10 Guinea pigs injected on day 0 with 0.5 ml vaccine and bled at 4, 8 and 12 weeks later.

FIG. 2 is a representation of mean antibody titers of groups of 10 Guinea pigs injected on day 0 with 0.5 ml vaccine and bled at 4, 8 and 12 weeks later.

DETAILED DESCRIPTION OF THE INVENTION

In the embodiment labeled FIG. 1, groups of 10 Guinea pigs were injected on day 0 with 0.5 ml vaccine and bled at 4, 8 and 12 weeks later. In the first panel, animals were injected with fresh liquid vaccine from the manufacturer (Medeva batch T022). The mean antibody titre in animals given fresh vaccine was higher than in the groups given dried vaccine, which suggests some loss of immunogenicity due to the drying protocol. Another 10 animals were injected with vaccine dried into a powder of sugar glass microspheres and rehydrated with water immediately before injection as indicated in the second panel. The third panel illustrates animals injected with vaccine dried into a powder of sugar glass microspheres suspended in 0.5 ml squalane oil. The fourth panel illustrates animals injected with vaccine dried into a powder of sugar glass microspheres suspended in 0.5 ml perfluorodecalin. Finally, in the fifth panel, animals were injected with a powder of sugar glass microspheres not containing vaccine suspended in 0.5 ml of squalane and in the sixth panel animals were injected with a powder of sugar glass microspheres not containing vaccine suspended in 0.5 ml of perfluorodecalin. While the antibody titre in the first two groups of animals injected with aqueous vaccines fell at 12 weeks after injection, the titre in the groups injected with vaccine in oil or PFC did not fall at 12 weeks. There was no antibody response in the fifth and sixth groups of animals injected with the vehicle formulation only.

FIG. 2 illustrates an embodiment where mean antibody titers of groups of 10 Guinea pigs were measured after they had been injected on day 0 with 0.5 ml vaccine and bled at 4, 8 and 12 weeks later. In the first panel, animals were injected with fresh liquid vaccine from the manufacturer which had been stored at 40° C. for 3 months. Another group of animals were injected with fresh liquid vaccine from the manufacturer which had been stored at 37° C. for 3 months, as indicated in the second panel. The third panel represents animals injected with vaccine dried into a powder of sugar glass microspheres, stored at 37° C. for 3 months and rehydrated with water immediately before injection. The fourth panel illustrates animals injected with vaccine dried into a powder of sugar glass microspheres and suspended in 0.5 ml squalane and stored in squalane at 37° C. for 3 months before injection. Finally, the fifth panel illustrates animals injected with vaccine dried into a powder of sugar glass microspheres and suspended in 0.5 ml perfluorodecalin and stored in PFC at 37° C. for 3 months before injection. In this particular embodiment, the antibody titer in animals given fresh vaccine was higher than in the groups given dried vaccine showing some loss of immunogenicity due to the drying protocol. While the antibody titer in the two groups of animals injected with aqueous vaccines which had been stored either wet or dry at 37° C. fell at 8 and 12 weeks after injection, the titer in the two groups injected with vaccine in oil or PFC rose progressively throughout the 12 weeks.

Experiments in vitro had suggested that PFCs might provide immediate release from glass microspheres suspended in them. They involved incorporating a water-soluble dye (Mordant Blue 9) in the sugar glass microspheres, and suspending them at 10% w/v in perfluorodecalin. When 0.5 ml of this opaque dark blue suspension was added to 1.5 ml of water, the PFC suspension fell to the bottom of the tube with the clear water layer on top. After vigorous vortex mixing for approximately one minute and standing for an additional minute, the overlaying water layer became intensely clear blue and the PFC layer cleared to water-white. The clearing of the opacity showed that the suspended particles in the PFC liquid had dissolved. The migration of the blue coloration from the PFC to the water layer showed that all of the hydrophilic dye had dissolved in the water as expected.

EXAMPLE 1

Using an easily assayed protein as a model vaccine confirms the above results. The enzyme alkaline phosphatase was chosen. The following solution was made:

Adjuvant grade calcium phosphate 10% w/v (Superphos Kemi a/s); Trehalose, 10% w/v; $ZnCl_2$, 1 mM; $MgCl_2$, 1 mM; Alkaline phosphatase, 20 U/ml in 5 mM Tris HCl buffer, pH 7.6.

The suspension was well mixed for 10 minutes at 37° C. to allow the insoluble calcium phosphate to adsorb the soluble alkaline phosphatase. This absorption was measured by centrifuging small aliquots of the suspension to deposit the calcium phosphate out of the suspension, sampling the supernatant solution and measuring its enzyme kinetics using p-nitrophenyl phosphate as substrate and a wavelength of 405 nm. The remaining suspension was then spray-dried to produce a fine powder. Any desorption of the enzyme after rehydration of the powder was measured in the supernatant as above. The powder was suspended at 20% w/v in perfluorophenanthrene and found to produce a stable suspension.

TABLE 1

| Sample Tested | Absorbance/min (405 nm) | % |
|---|---|---|
| Orginal solution (25 ul) | 0.409 | 100 |
| Supernatant (25 ul) from above | 0.034 | 8 |
| Rehydrated powder (25 ul of a 20% w/v in water) | 0.425 | 104 |
| Supernatant from above (25 ul) | 0.004 | 1 |
| 20% w/v powder in PFC (25 ul) | 0.430 | 105 |

Thus 92% of the enzyme was adsorbed to the calcium phosphate adjuvant (Table 1). All of this enzyme was eventually recovered for an assay of enzyme activity after being suspended in PFCs in trehalose glass microspheres. These were re-dissolved in water as in the blue dye example above.

This experiment suggested that glass microspheres suspended in PFCs dissolved rapidly when mixed with water in vitro, indicating that these preparations would also release their antigen rapidly in vivo. This is apparently not the case. Surprisingly, there seems to be a slow, controlled release of antigen over a considerable period of time after injection. The release of antigen in this system is similar to that thought to occur with certain oil-based adjuvant liquid emulsions used in animals, such as Freund's Complete Adjuvant. It is thought that the slow leaking of the antigen from the droplets of antigen solution dispersed in the mineral oil deposit of Freund's adjuvant is responsible for the greatly augmented immune responses found in animals immunized in this way. [(Freund J. Some aspects of active immunization. *Ann. Rev. Microbiol* 1 291 (1947).] Similar results have been found after immunization with antigens stabilized in sugar glass microspheres suspended in anhydrous biocompatible liquids. A major difference between Freund's adjuvant and the present system is that the former is a liquid emulsion of aqueous antigen solution droplets in oil and therefore inherently unstable while the latter is a stabilized dry solid in a glass microsphere suspension and therefore inherently stable. In addition, Freund's adjuvant is a violent irritant and unacceptable for use in humans [(Immunological adjuvants report of a WHO scientific group meeting held in Geneva from Oct. 6 to 10, 1975) 1976] while the PFC formulation used herein is non-toxic. It causes neither immediate nor delayed irritation or inflammation after injection. It is therefore ideally suited to the development of a single-dose vaccine for use in humans, especially in children, where its lack of irritation is an additional bonus. The ability of these formulations to control the release of actives stabilized in soluble glass microspheres is not of course restricted to vaccines. A wide variety of other drugs require repeated injections for their therapeutic efficacy. Indeed it is exceptional for a parenteral drug to be effective in a single dose. In each case the rate of release of the active molecule from solid solution in the soluble glass into free solution in the body fluids would need to be accurately controlled and would be different for each different active molecule.

While various anhydrous biocompatible liquids can be used in this system, PFCs are preferred because of their great chemical and physical stability, their lack of toxicity, their low viscosity and surface tension and their high density.

TABLE 2

Physicochemical properties of some perfluorocarbons.

| PFC | MW | Density (Kg/L) | Viscosity (mPas) | Surface Tension (mN/m) | Vapor Pressure (mbar) |
|---|---|---|---|---|---|
| hexane | 338 | 1.68 | 0.66 | 11.10 | 294 |
| n-octane | 438 | 1.73 | .127 | 16.98 | 52 |
| decalin | 462 | 1.92 | 5.10 | 17.60 | 8.8 |
| phenanthrene | 624 | 2.03 | 28.40 | 19.00 | <1 |

A wide variety of PFC liquids can be obtained depending on the particular parent hydrocarbon molecule that is fluorinated. It is likely that the rate of absorption from the tissues into the bloodstream, and of removal from the body in the exhaled breath is a function of the vapor pressure of the PFC at body temperature. This is in turn generally proportional to molecular weight (Table 2). By carefully choosing a particular PFC, it is likely that the rate of controlled release can be varied over a substantial range. Since the PFC liquids can also be blended together, the release rates can be precisely fixed by choosing an appropriate mixture of PFC liquids.

Calcium phosphate, used as a density matching agent, is insoluble in water and forms a fine, highly-hydrated colloidal suspension which is able to reversibly bind large amounts of macromolecules, especially proteins, from solution. A significant proportion of the antigen present in the tetanus toxoid vaccine used in these studies was bound to both the aluminum hydroxide adjuvant originally used in the vaccine and to the calcium phosphate suspension used as a density matching substance. The protein antigens bound to these inorganic colloids act as a reservoir for the sustained release seen in the animal studies. The degree of delay in the release profile seems to be much greater when the vaccine is in suspension in PFC liquids than with the aqueous suspension, used as a control. This suggests that the non-aqueous PFC liquid is the critical component in controlling the rate of release from the inorganic colloids. It will require further experimentation to establish whether equally sustained release from PFC liquids can occur if the protein is free in solid solution in the glass microspheres rather than bound to an inorganic colloid.

The use of calcium phosphate in these formulations has additional advantages over and above the matching of the density of the sugar glass microspheres with the PFC liquids. Since the inorganic fraction of bone itself consists of calcium phosphate in the form of hydroxyapatite, the chemistry of this additive is biocompatible and non-toxic. It is safe to assume that calcium phosphate injected in this way will be locally non-toxic and will be slowly solubilized from the injection site and/or the regional draining lymph nodes eventually, leaving no excess.

Before this occurs, the deposit of calcium phosphate at the injection site acts as a positive marker of immunization, which is detectable by medical imaging techniques, such as x-rays or MRI, or even possibly by ultrasound or magnetometry. The ability to positively identify patients who have been immunized is sometimes of real importance in disease eradication programs where local record keeping is imperfect and patients' knowledge of their own immunization history may be incomplete. By substituting other density-regulating materials such as barium sulphate, titanium dioxide and other insoluble and dense inorganic precipitates or defined mixtures of them, it may be possible to uniquely mark different vaccines with separate density matching chemicals. Then an accurate immunization history may be detectable by relatively superficial medical imaging or detection methods.

While there has been described what are believed to be the preferred embodiments of the present invention, those skilled in the art will recognize that other and further changes and modifications may be made thereto without departing from the spirit of the invention, and it is intended to claim all such changes and modifications as fall within the true scope of the invention.

What is claimed is:

1. A pharmaceutical composition comprising a drug selected from the group consisting of hormones, analgesics, narcotics, narcotic antagonists, chemotherapeutics, immunosuppressants, immunomodulators, contraceptives, vasoactive agents, coagulation modifiers, cardioactives, anti-inflammatories, and CNS drugs to be injected into a patient wherein, the drug is in soluble glass composite microspheres of sugar and calcium phosphate and the soluble glass composite microspheres are suspended in a biocompatible anhydrous liquid whereby the drug is protected against dissolution while remaining surrounded by anhydrous liquid thereby, extending the duration of action of the drug long after injection by slowly releasing the drug or vaccine into the patient's circulatory system.

2. The pharmaceutical composition according to claim 1 wherein said vaccine is selected from a group consisting of toxins, toxoids, live or killed bacteria, live or killed viruses, live or killed protozoa, recombinant proteins, DNA, RNA, polysaccharides, lipoproteins and lipids and recombinant or synthetic peptides.

3. The pharmaceutical composition according to claim 1 wherein said soluble glass microspheres are selected from a group consisting of non-reducing sugars and sugar alcohols, metal carboxylates and phosphate glasses.

4. The pharmaceutical composition according to claim 3 wherein said non-reducing sugars are selected from the group consisting of sucrose, trehalose, raffinose, and stachyose.

5. The pharmaceutical composition according to claim 3 wherein said sugar alcohols are selected from the group consisting of mannitol, arabinitol, inositol, glucitol, galactitol, xylitol, maltitol, lactitol, glucopyranosyl sorbitol and glucopyranosyl mannitol.

6. The pharmaceutical composition according to claim 1 wherein said anhydrous biocompatible liquid is selected from a group consisting of anhydrous hydrophilic liquids, anhydrous hydrophobic liquids, anhydrous silicone fluids or anhydrous perfluorocarbons.

7. The pharmaceutical composition according to claim 1 wherein said glass composite microspheres contain an amount of an insoluble biocompatible high-density agent sufficient to raise the average density of the microspheres to match that of the anhydrous biocompatible liquid in which they are suspended.

8. The pharmaceutical composition according to claim 7 wherein said insoluble biocompatible high-density agent is selected from the group consisting of calcium phosphate, aluminum phosphate, aluminum hydroxide, barium sulphate and titanium dioxide.

9. The pharmaceutical composition according to claim 1, wherein said vaccine is tetanus toxoid.

10. The pharmaceutical composition according to claim 9, wherein said vaccine is adsorbed to an adjuvant.

11. The pharmaceutical composition according to claim 10, wherein said adjuvant is selected from a group consisting of aluminum hydroxide, aluminum phosphate or calcium phosphate.

12. The pharmaceutical composition according to claim 9, wherein a suspension of calcium phosphate colloidal gel is added to a solution of trehalose, zinc chloride, magnesium chloride, and Tris buffer which is added to aid in the formation of a stabilized tetanus toxoid in said glass microspheres.

13. The pharmaceutical composition according to claim 12, wherein said solution is spray-dried to a fine-powder.

14. The pharmaceutical composition according to claim 13, wherein said powder is suspended in perfluorocarbon to produce a stable suspension.

15. The pharmaceutical composition according to claim 14, wherein said perfluorocarbon is selected from a group consisting of perfluorohexane, perfluorodecalin, perfluorooctane and perfluorophenanthrene.

16. A method of formulating a drug or vaccine to prolong the duration of action when administered in an effective amount, which drug or vaccine is formulated by:

incorporating said drug or vaccine in soluble glass composite microspheres suspending said soluble glass composite microspheres in a biocompatible anhydrous liquid whereby said drug or vaccine is protected against dissolution while remaining surrounded by anhydrous liquid thereby slowly releasing the drug or vaccine into the patient's circulatory system.

17. The method of claim 16 including the step of producing the soluble glass composite microspheres is selected from the group consisting of spray-drying, air drying, vacuum drying, emulsion solidification, precipitation, and melting and grinding to a fine powder.

18. The method of claim 17 wherein said fine powder is suspended in the anhydrous biocompatible liquid which is a perfluorocarbon.

19. The method of claim 18 wherein said perfluorocarbon is selected from the group consisting of perfluorohexane, perfluorodecalin, perfluorooctane and perfluorophenanthrene.

* * * * *